(12) United States Patent
Sun

(10) Patent No.: US 7,042,556 B1
(45) Date of Patent: May 9, 2006

(54) DEVICE AND NONDESTRUCTIVE METHOD TO DETERMINE SUBSURFACE MICRO-STRUCTURE IN DENSE MATERIALS

(75) Inventor: Jiangang Sun, Westmont, IL (US)

(73) Assignee: The United States of America as represented by the United States Department of Energy, Washington, DC (US)

( * ) Notice: Subject to any disclaimer, the term of this patent is extended or adjusted under 35 U.S.C. 154(b) by 182 days.

(21) Appl. No.: 10/731,772

(22) Filed: Dec. 5, 2003

(51) Int. Cl.
*G01C 3/08* (2006.01)

(52) U.S. Cl. .................. 356/4.07; 356/3.01; 356/5.01; 356/237; 356/239; 356/369

(58) Field of Classification Search .............. 356/4.07
See application file for complete search history.

(56) References Cited

U.S. PATENT DOCUMENTS 3,633,212 A * 1/1972 Cooper .................... 346/107.2
5,689,332 A * 11/1997 Ellingson et al. ......... 356/237.1
5,745,236 A * 4/1998 Haga ......................... 356/600
6,285,449 B1 * 9/2001 Ellingson et al. ......... 356/237.1

OTHER PUBLICATIONS

H. R. Hee, et al. "Optical Coherence Tomography for Ophthalmic Imaging", IEEE Engineering in Medicine and Biology, 95 Sun ,et al., "Application. of Optical Scattering Methods to Detect Damage in Ceramics", in Machining of Ceramics and Composites, Part IV; Chapter 19, edited by Jahanmir et al., in 1999, 1t 669.
Zhang et al., "Subsurface Damage Measurement In Silicon Wafers By Laser Scattering", in Transactions of NAMSI/SME, vol. XXX, 2002, at 535.

* cited by examiner

*Primary Examiner*—Thomas H. Tarcza
*Assistant Examiner*—Luke Ratcliffe
(74) *Attorney, Agent, or Firm*—Micahel J. Dobbs; Brian J. Lally; Paul A. Gottlieb

(57) ABSTRACT

A method and a device to detect subsurface three-dimensional micro-structure in a sample by illuminating the sample with light of a given polarization and detecting light emanating from the sample that has a different direction of polarization by means of a confocal optical system.

20 Claims, 6 Drawing Sheets

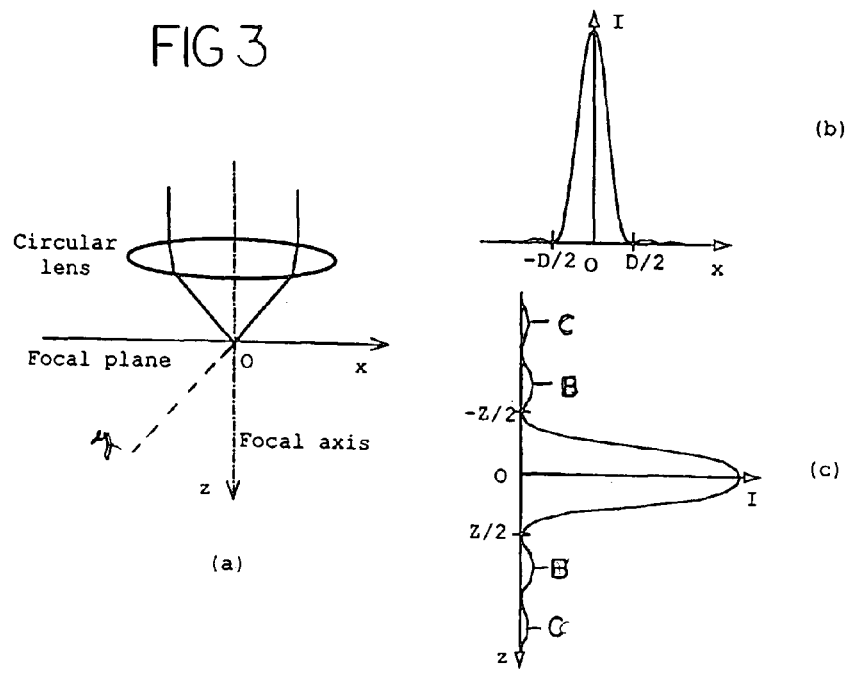
FIG 3
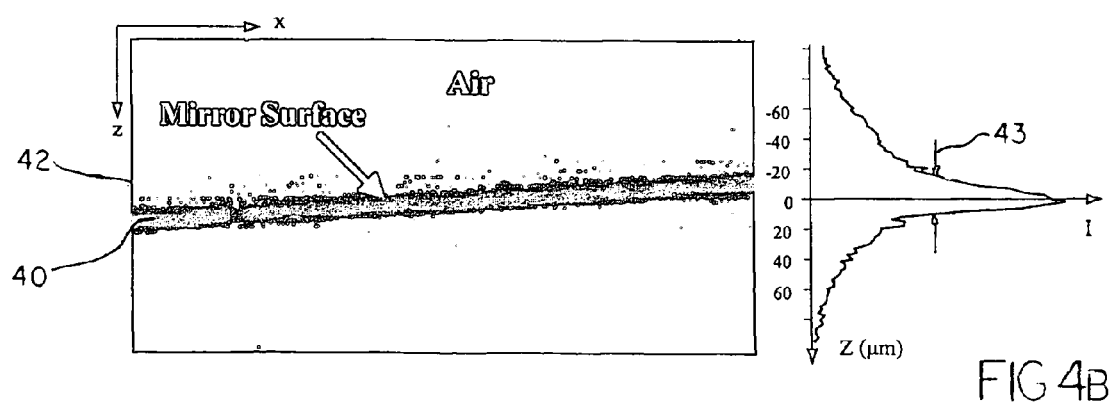
FIG 4A
FIG 4B

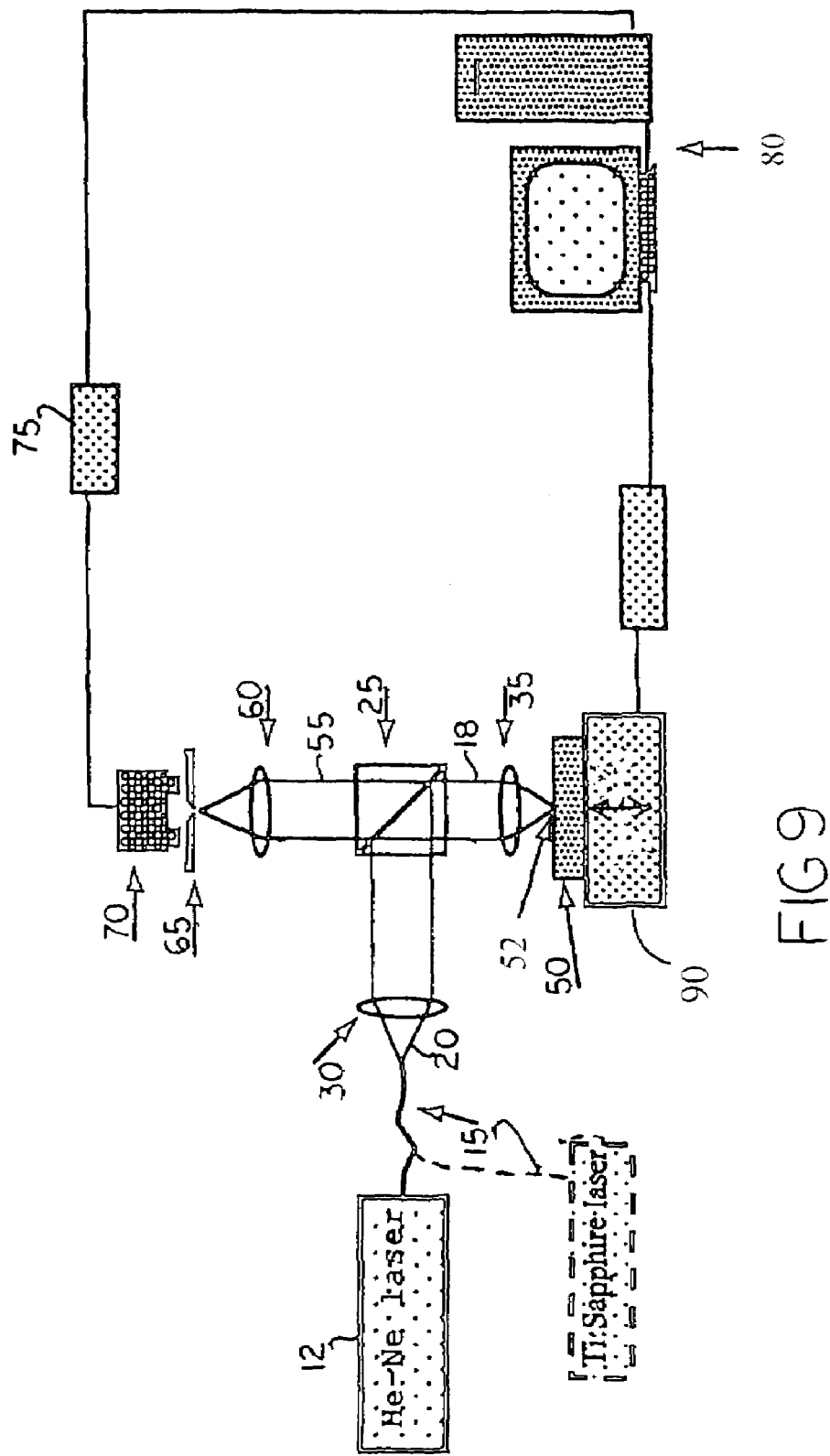

DEVICE AND NONDESTRUCTIVE METHOD TO DETERMINE SUBSURFACE MICRO-STRUCTURE IN DENSE MATERIALS

BACKGROUND OF THE INVENTION

1. Field of the Invention

The present invention relates to the field of confocal microscopy and, more particularly, the present invention relates to high three-dimensional resolution cross-polarization devices for imaging subsurface micro-structure.

2. Description of the Prior Art

Measurement of detailed subsurface micro-structure is critical in determining properties of materials and understanding material processing mechanisms. At present, subsurface micro-structure is typically examined by destructive methods such as: (a) cutting the sample to examine cross-sectional micro-structure; (b) polishing or removing surface layers to examine micro-structure at layers of different depths; (c) cutting or polishing the sample at an angle to the surface. Destructive examination has several disadvantages, including being time consuming, error prone, and inapplicable for live tissues.

Non-destructive methods (such as microscopy) for examining sub-surface detail of materials have been explored. However, most microscopic methods, including optical microscopy, can only examine the 2D micro-structure of the specimen's surface. This is so because when light is incident on a surface, the majority of the light coming back for measurement originates from the surface, unless the material is transparent. For example, during the examination of metals, only surface reflection and scattering occur.

For translucent materials such as ceramics, silicon, and biological materials, a portion of the incident light may penetrate into the material subsurface. A fraction of this penetrating light is back-scattered due to interactions with the internal micro-structure. This back-scattered light may escape back from the surface and be detected (See FIG. 1). Internally back-scattered light is, however, very weak compared with the light incident on the surface.

By selective detection of only the internally back-scattered light, the subsurface micro-structure can be determined. One technique to detect and resolve depth of the internal back-scattering is optical coherence tomography (OCT). The technique is based on low-coherence optical gating of the back-scattered light from different depths relative to a reference beam using an interferometer. Interference occurs when the scattering depth is equal to a reference "depth" which is determined by the position of a reflector. Low coherence of the light being used ensures a narrow gating of the depth range and therefore high resolution. By moving the reflector and synchronously measuring the interference signal, the scattering data from various depths can be obtained. Typical depth resolution is larger than 10 μm. (See H. R. Hee et al. "Optical Coherence Tomography for Ophthalmic Imaging," IEEE Engineering in Medicine and Biology, 1995, at 67).

Another method to separate surface reflection/scattering from subsurface scattering is to use the polarization properties of light. In the plane perpendicular to the direction of light travel, the electric field of the light can be described as having two perpendicular components which are referred to, for example, as vertically-polarized and horizontally-polarized components when the plane is vertical. When incident light is linearly polarized (i.e., with only one polarization component), the surface reflected or scattered light typically has the same polarization as the incident light. The subsurface scattered light, however, may become completely depolarized (i.e., with equal intensity in both polarization directions) because of multiple interactions with the subsurface micro-structure. When one uses polarized optics to selectively detect the cross-polarized light (i.e. light polarized perpendicular to the polarization of the incident light) that is due to subsurface back-scattering, the detector signal is related only to subsurface micro-structure variation. Methods based on this principle have been successfully used to detect subsurface defects in ceramic and silicon materials, and for biological tissue. However, because the detector receives cross-polarized back-scattered light from all subsurface depths, this method has no depth resolution and typically yields only 2D images.

Confocal microscopy with 3D resolution has been widely used to examine biological materials such as cells and tissues. The method uses a point source and a point detector; both at the focal points of an objective lens which is focused on a sample. When high numerical aperture (NA) objectives are used, 3D spatial resolution (including depth) can be achieved well below a micrometer. This method is usually used to examine semi-transparent biological materials prepared with a fluorescent dye. The method is also used to examine the topology of semiconductor devices using the superb depth resolution of confocal microscopy. However, this method cannot be used to examine subsurface micro-structure of dense materials such as ceramics.

A need exists in the art for a method and a device to obtain high-resolution three-dimensional information concerning the subsurface micro-structure of dense materials such as ceramics.

SUMMARY OF THE INVENTION

It is an object of the present invention to provide a method and a device to obtain high-resolution three-dimensional information concerning the subsurface micro-structure of dense materials that overcome the disadvantages of the prior art. Generally speaking, 'dense' materials are materials that are optically translucent but not transparent.

Another object of the present invention is to provide a method and a device to obtain high-resolution three-dimensional information concerning the subsurface micro-structure of dense materials such as ceramics. A feature of the present invention is that only light emanating from below the surface of the sample is detected. An advantage of the present invention is that a method and a means are provided to exclude light emanating from the surface of the sample which would mask the signal from subsurface structures.

It is another object of the present invention to provide a non-destructive method and device to obtain high-resolution three-dimensional information concerning the subsurface micro-structure of dense materials. A feature of the present invention is to combine cross-polarization/subsurface back-scattering detection with scanning confocal microscopy. An advantage of the present invention is that the sample is subjected only to light, therefore no destructive effects on delicate samples such as living tissues occur. Another advantage is that the invention provides micro-structure detail at each of various levels below the surface of a substrate.

Briefly, the present invention provides a method for depth-resolved detection of subsurface micro-structure and features in a sample (said features including air pockets, fault lines, interfaces, and porosity) by illuminating a location or spot on the sample with light polarized in a given direction and measuring the intensity of back-scattered light in another direction of polarization as a function of the x,y,z coordinates and of the orientation of the illuminated spot on the sample. In more detail, the invented method comprises: allowing positioning and orienting of the sample in all directions; illuminating a first spot on the sample with incident light that is linearly polarized in a given direction of polarization; detecting light emanating from the sample that is linearly polarized in a direction distinct from the direction of polarization of the incident light; illuminating a second spot by moving said sample or said light in one or more directions; and measuring variation in the intensity of the light emanating from the sample as the illuminating light is moved from the first spot to the second spot. The process is repeated by changing the position of the illuminated spot in all three dimensions. Also, provision is made for rotating the sample in all directions so that the illuminating light would strike the sample at a series of angles.

Also the present invention provides a device for depth-resolved detection of subsurface micro-structure and features in a sample, said features including air pockets, fault lines, interfaces, and porosity and said device comprising: an initial beam of light polarized in a first direction; means to deflect said beam towards a first spot on a sample which is mounted on a stage that is movable in one or more directions; means to select light emanating from said first spot when said emanating light has a second direction of polarization; means to move said sample relative to the deflected beam so that said deflected beam is directed to a second spot; and a means to measure variations in the light intensity emanating from said spots.

BRIEF DESCRIPTION OF THE DRAWING

The foregoing invention and its advantages may be readily appreciated from the following detailed description of the invention, when read in conjunction with the accompanying drawing in which:

FIG. 3a illustrates focusing of a parallel beam by a circular lens;

FIG. 3b illustrates the intensity profile in the focal plane of a parallel beam focused by a circular lens;

FIG. 3c illustrates the intensity profile along the focal axis of a parallel beam focused by a circular lens;

FIG. 4a is a scan image of a mirror sample taken with a 20× objective using a first embodiment of a non-polarized device for depth-resolved detection, in accordance with features of the present invention;

FIG. 4b is an intensity profile taken of the mirror sample in FIG. 4a, in accordance with features of the present invention;

FIG. 9 is a schematic diagram of a second embodiment of a method and device for depth-resolved detection of subsurface micro-structure and features by combining cross-polarization/subsurface-back-scattering detection with a scanning confocal system, in accordance with features of the present invention.

DETAILED DESCRIPTION OF THE INVENTION

Figure 1:
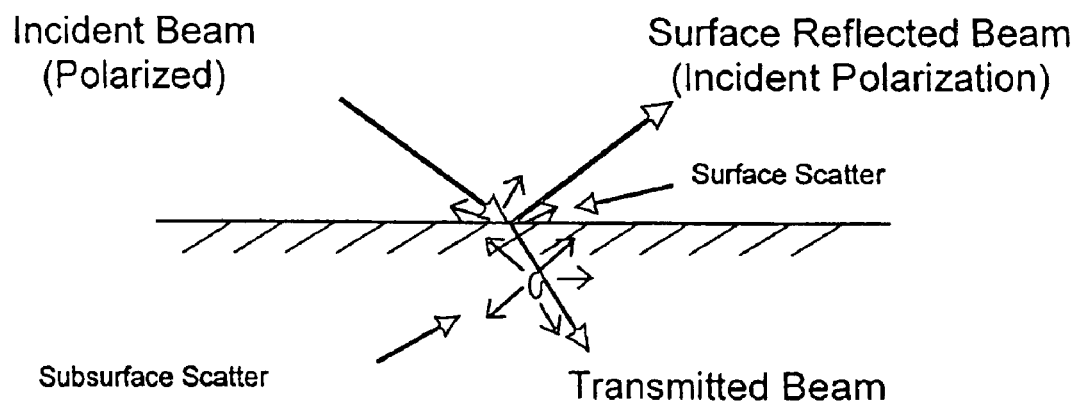
FIG. 1 is a schematic diagram depicting reflection and scattering of light from surface and sub-surface structures in a material.

The present invention comprises a new method and device for depth-resolved detection of subsurface micro-structure and other features in dense materials. The materials the micro-structure of which can be studied with the present method and device include translucent materials such as ceramics, ceramic composites, ceramic coatings, silicon, semiconductors, and biological materials. Examples of subsurface structure that can be detected include air pockets, fault lines, the presence of different grain sizes, changes in porosity, interfaces between different structures/materials, etc. . . . These structures exhibit enhanced back scattering of the incident light.

The invention utilizes cross-polarization detection of subsurface back-scattering with a scanning confocal system to achieve depth resolution of translucent materials. The depth that can be reached depends on the sensitivity of the detector. With a semi-conductor detector one may detect the back-scatter from a depth that is more than four times the optical skin depth of the material (the "skin depth" is usually defined as the depth where the transmitted light intensity is reduced to $e^{-1}$, or about 37%, of the incident light intensity at the surface). When a photo multiplier detector is utilized, depths 80 percent deeper can be analyzed.

Generally, the method and device facilitates the production of high spatial-resolution 3D images of subsurface micro-structure of substrates by scanning in the 2D surface plane and in the depth direction. A first embodiment of the method and the device is illustrated schematically in FIG. 2 as numeral 10. A laser 12 delivers a beam polarized in a first direction (in what is here defined as the vertical direction) by means of a suitable polarization-maintaining optical fiber 15 with a diameter ranging typically between 1 and 10 microns. A suitable laser to be utilized as a light source is a HeNe laser of wavelength of 633 nm. Polarized lasers with other wavelengths, such as a Ti:Sapphire laser with a tunable wavelength of 0.7–1 micron, can also be used. Because the fiber 15 is very thin (i.e. 4 μm in diameter; this fiber should be as thin as possible, preferably a few microns), light exiting from the fiber can be considered to be emanating from a point source 20. The diameter of the fiber that is used is a function of the laser intensity and the resolution desired while the fiber preserves the light polarization. Such fibers are widely commercially available for example through Newport Corp., Irvine, Calif.

The light from the point-like source is expanded by a lens 30. Except for the use of a polarized beam-splitter (PBS) 25, the rest of the device is typical of a conventional confocal device. The vertically-polarized beam emanating from the lens 30 is reflected at some suitable angle (for example 90 degrees) by the PBS and focused on a sample 50 by an objective lens 35.

A back-scattered beam 18 is collected by the objective lens 35 and directed back to the PBS. The PBS allows only cross-polarized light scattered from the subsurface of the illuminated sample region to pass through to the detection path 55 (the surface-reflected/scattered light has the same polarization as the incident beam and is therefore reflected back to the optical fiber). The cross-polarized light is defined as light polarized in a second direction of polarization (usually 90 degrees from the first polarization direction). As defined here, this light is horizontally polarized.

The cross-polarized light is then focused by an imaging lens 60 onto a pinhole aperture 65 and the intensity of the light within the aperture is measured by a detector 70. The size of the aperture is a function of the resolution desired. Pinhole apertures from 1 to more than 100 microns in diameter have been used in conventional confocal microscopes. Generally, the imaging lens is situated intermediate to the PBS and the pinhole. The above components are maintained in rigid relation to each other by mounting them on an optical table or a set of optical benches.

The detector signal is processed by an optical power meter 75. The optical power meter converts the detector output into a signal that is provided to and recorded in a database residing in a personal computer 80. The computer controls the x-y-z translation stage 85 whereon the sample is mounted. During a typical test, the sample is scanned in the x-y-z directions in a raster fashion (i.e. along closely spaced parallel straight lines), and the resulting 3D optical-scattering image data are related to the subsurface micro-structure of the sample. The method described above is often referred to as CPCM (Cross-Polarization Confocal Microscopy). The cross-polarization-scattering detection method is described in Sun et al. [J. G. Sun, W. A. Ellingson, J. S. Steckenrider, and S. Ahuja, "Application of Optical Scattering Methods to Detect Damage in Ceramics," in *Machining of Ceramics and Composites*, Part IV: Chapter 19, eds. S. Jahanmir, M. Ramulu, and P. Koshy, Marcel Dekker, New York, pp. 669–699, 1999; .M. Zhang, J. G. Sun, and Z. J. Pei, "Subsurface Damage Measurement in Silicon Wafers by Laser Scattering," *Trans. NAMRI/SME*, Vol. XXX, pp. 535–542, 2002; W. A. Ellingson, J. A. Todd, and J. G. Sun, "Optical Method and Apparatus for Detection of Defects and Microstructural Changes in Ceramics and Ceramic Coatings," U.S. Pat. No. 6,285,449 (2001)]. All of these references are incorporated in this specification by reference.

Also, while observation of light emanating from the sample that is polarized orthogonally to the incident light has the highest ratio of intensity emanating from the subsurface to intensity from the surface, one may choose to detect light emanating from the sample that is polarized in another direction that is distinct from that of the incident light.

Confocal optical imaging was demonstrated experimentally to obtain superior spatial resolution by eliminating contributions from out-of-focus illuminations. The inventor achieved this by first supplying a high-quality light source, i.e., a point source 20, so that a significant portion of the light is focused by the objective lens 35 into a small (diffraction limited) spot 52 in the sample 50. A spatially-restricted point detector 70 (i.e a detector placed downstream from a point aperture) is further used to detect only the light emanating from the focus spot 52. The spatial resolution of the confocal apparatus is limited only by the size of the focus spot which size is determined by the numerical aperture (NA) of the objective lens.

For a well-corrected objective lens (i.e., one without lens aberrations), its focus-spot size is calculated from diffraction theory. For a circular objective, the normalized intensity profiles of light in the focal plane (x-y plane, although the profile is plotted along x direction because it is axisymmetric) and along the optical axis (z direction) are plotted in FIG. 3. It is seen that the intensity (I) reduces from the maximum at the focal point (point O) to zero in short distances both in the focal plane and along the focal axis. The diameter between the first zero-intensity points at either sides of point O in the focal plane is $$D=1.22\lambda/n(NA)$$

where $\lambda$ is the wavelength of the light, n is material's refractive index (n=1 for air), and (NA) is the numerical aperture of the lens. The distance between the first zero-intensity points in the focal axis direction is $z=4\lambda/n(NA)^2$. In practice, the lateral resolution in the focal plane has been defined as:

$$\Delta r=0.61\lambda/n(NA), \qquad (1)$$

i.e. $\Delta r=D/2$, and the depth resolution in the focal axis as:

$$\Delta z=2\lambda/n(NA)^2 \qquad (2)$$

It should be emphasized that while conventional confocal imaging detects light emanating directly from the focused spot as it travels through transparent or semi-transparent media, the current method detects cross-polarized back-scattered light that has interacted many times with the material's internal micro-structure. As noted supra, this interaction produces a change in the polarization direction from that of the incident beam. The focused spot within the material may be slightly larger due to multiple interactions but should be comparable to that in line-of-sight type of detection in conventional methods because the spot size can never become infinitely small as stipulated by geometrical optics but is of a finite size as determined by the diffraction limit.

Another feature of the present method is that it can achieve better subsurface detection sensitivity than that of the OCT in spite of the fact that both methods measure the intensity of the back-scattered light that is produced due to a material's micro-structure variations. With low NA lenses, this inventor has demonstrated depth resolution of 4 μm. However, depth resolution by confocal imaging can achieve 0.2–0.3 μm by using higher NA lenses (see Eq. 2), while the depth resolution of typical OCT method is 10 μm. In addition, CPCM sensitivity is not affected by strong surface reflection or scatter while surface reflection/scatter may prevent OCT from detecting near-surface features.

Figure 2:
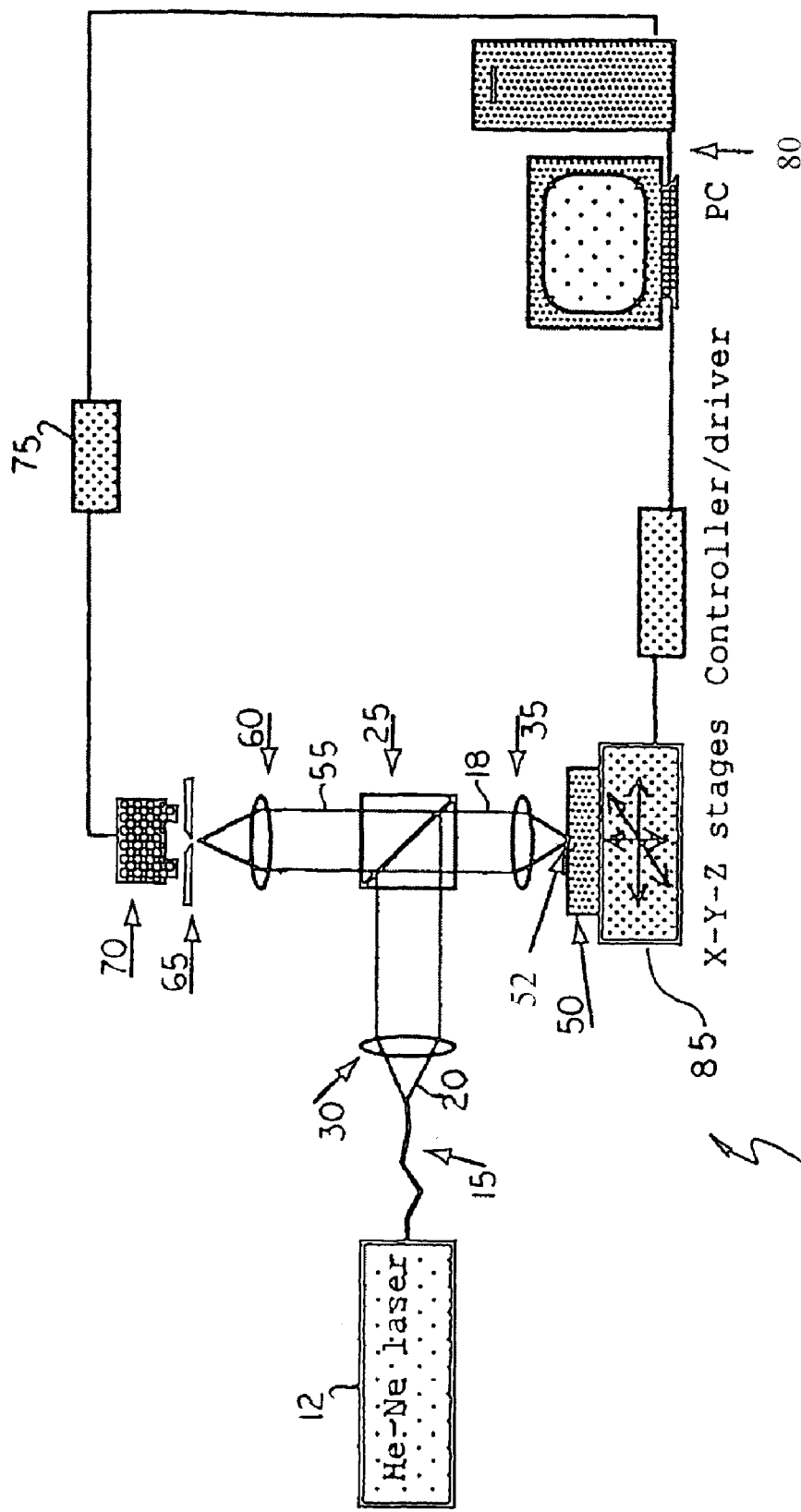
FIG. 2 is a schematic diagram of a first embodiment of a method and device for depth-resolved detection of subsurface micro-structure and features, in accordance with features of the present invention.

CPCM is applicable to all materials that are optically translucent (i.e., where light can penetrate to a depth below the surface) or semitransparent. Such materials include, but are not limited to: (a)ceramics, ceramic coatings, ceramic composites; (b) silicon wafers, semiconductor wafers, silicon or semiconductor integrated circuits (IC's);(c) biological materials and tissues. Optical penetration in these materials can be from tens of microns to several millimeters deep. Given that the invented method allows detection of back-scattered radiation from regions deeper than four skin-depths it is advantageous to program the computer so that the detected value of every pixel is multiplied by a factor of $e^{2\alpha}$ according to its z-position in the image data, where $\alpha$ is the linear attenuation coefficient of the sample material so as to compensate for intensity decay in the back-scattered light within the subsurface Sample Results An exemplary embodiment of a cross-polarization confocal-imaging system is depicted in FIG. 2. A polarized He—Ne laser with wavelength of 0.633 µm was used. The vertically-polarized laser beam was directed to a polarization-maintaining optical fiber of 4 µm in diameter. Light exits from the fiber as if from a point-like source and is expanded by a lens to a parallel beam (an optical setup with non-parallel beams can also be used). A polarized-beam-splitter (PBS) cube directs the parallel beam to a 20× microscope objective lens (NA=0.4) which focuses the beam into the sample subsurface. The cross-polarized back-scattered light passes through the PBS cube and is focused by a microscope objective onto a 5-µm-diameter pinhole aperture and measured by a semiconductor optical detector. As illustrated in FIG. 2, the system also includes an optical power meter to measure the intensity of the detected light, a PC, and x-y-z linear-translation stages with a stage controller/driver controlled by the PC.

Figures 5A, 5B:
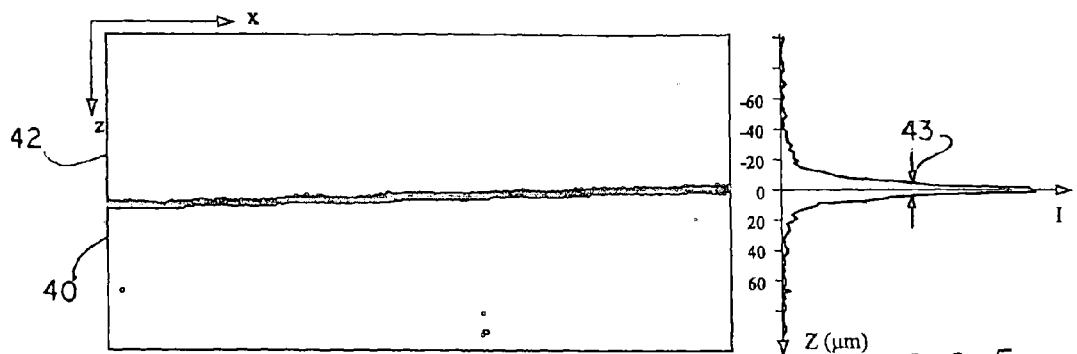
FIG. 5a is a scan image of a mirror sample taken with a 40× objective using a first embodiment of a non-polarized device for depth-resolved detection, in accordance with features of the present invention.
FIG. 5b is an intensity profile along depth taken of the sample in FIG. 5a, in accordance with features of the present invention.

To assess such a system's alignment and its performance on depth resolution, it is a common practice to scan a mirror or some other well-defined reflection surface. The result of such an assessment for the present invention is depicted in FIG. 4. To conduct this test, the PBS cube is replaced by a non-polarizing 50/50 beam-splitter cube while the rest of the system is unchanged. A mirror 40 is scanned in the x-z plane where x-direction is parallel to the mirror surface 42 and z-direction is normal to the mirror surface. The scan-step size in both x and z directions was 2 µm. FIG. 4 shows the scan image (note that there is a small angle in the alignment of the mirror surface) and a line profile of the data in the z-direction. The intensity (I) is maximum at the mirror surface. The half-width at half-maximum (HWHM) 43 is determined to be 12 µm, which is slightly larger than the estimated resolution from Eq. (2) (i.e., 8 µm) for the 20× objective. The scan image and depth-profile data obtained with a 40× objective (NA=0.65) are shown in FIG. 5, and the measured HWHM of 4 µm is consistent with the estimate of Δz=3 µm from Eq. (2). The worse depth resolution than that theoretically predicted is due to lens aberrations and other inefficiencies and, in the 20× objective case, a slight misalignment.

Figure 6:
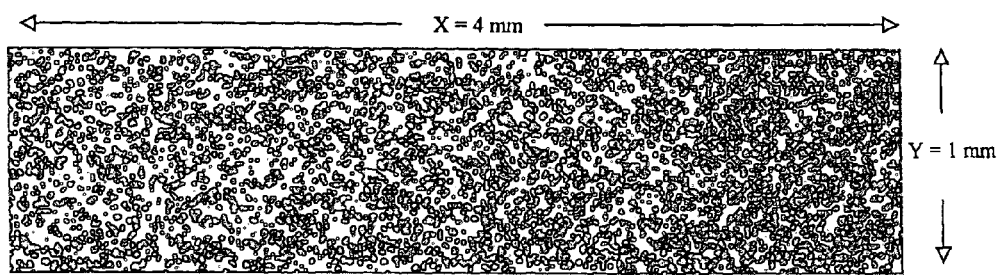
FIG. 6 is a cross-polarization subsurface x-y scan image for a silicon-nitride ceramic taken with a conventional cross-polarization device.

The system was used to scan a monolithic silicon-nitride ceramic. This material is generally dense but contains strong-scattering regions/spots (due to higher porosity or differing material structure) distributed throughout the volume. FIG. 6 shows a 2D x-y subsurface-scan performed with the x-y plane parallel to the sample surface and the image obtained with a cross-polarization-scattering detection method described in Sun et al. [J. G. Sun, W. A. Ellingson, J. S. Steckenrider, and S. Ahuja, "Application of Optical Scattering Methods to Detect Damage in Ceramics," in *Machining of Ceramics and Composites*, Part IV: Chapter 19, eds. S. Jahanmir, M. Ramulu, and P. Koshy, Marcel Dekker, New York, pp. 669–699, 1999; .M. Zhang, J. G. Sun, and Z. J. Pei, "Subsurface Damage Measurement in Silicon Wafers by Laser Scattering," *Trans. NAMRI/SME*, Vol. XXX, pp. 535–542, 2002; W. A. Ellingson, J. A. Todd, and J. G. Sun, "Optical Method and Apparatus for Detection of Defects and Microstructural Changes in Ceramics and Ceramic Coatings," U.S. Pat. No. 6,285,449 (2001)]. All of these references are incorporated in this specification by reference. It is seen that strong-scattering spots are distributed in the subsurface, but their depths below the surface cannot be determined.

Figure 7:
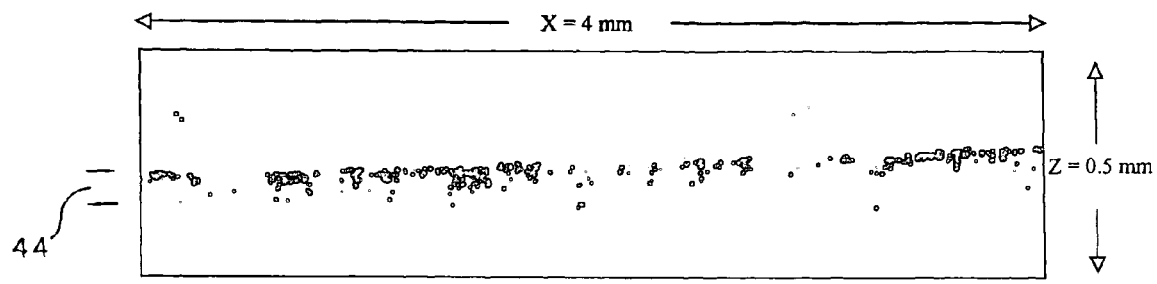
FIG. 7 is a cross-polarization confocal x-z scan image for the silicon-nitride ceramic sample of FIG. 6 taken with a first embodiment of a device in accordance with features of the present invention.

FIG. 7 shows an x-z scan image obtained using the invented cross-polarization confocal system. By conducting additional x-z scans in the y-direction, 3D images of the subsurface can be obtained. The scan-step size in the x direction was 10 µm and in the z (depth) direction 5 µm. Along the x-direction parallel to the surface, the size and distance distribution of the strong-scattering spots are consistent with those observed in the x-y scan image in FIG. 6, but now their extensions in the depth z-direction are also determined. The signal intensity, however, reduces to noise level at an apparent depth 44 of about 100 µm.

Suitable optical detectors include, but are not limited to photomultiplier tubes (PMT), semiconductor detectors, etc. A PMT is typically 2–3 orders of magnitudes more sensitive than the semiconductor optical detector used in this prototype for the invented system. Had a PMT been used, detection could have been extended to deeper regions into the subsurface, up to 180 µm.

Figure 8:
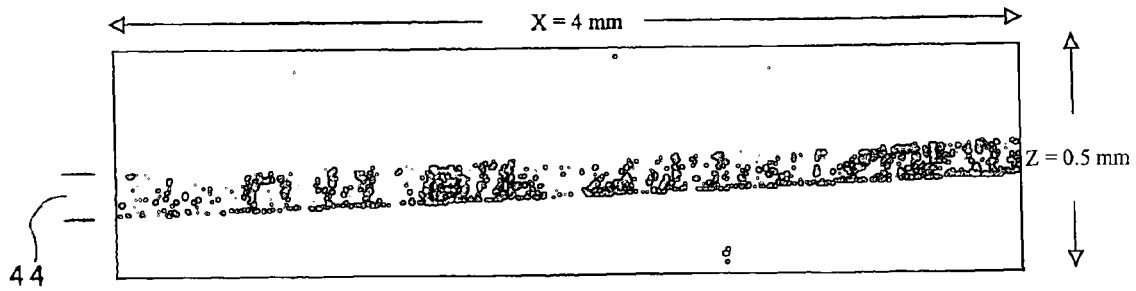
FIG. 8 is the cross-polarization confocal x-z scan image for the silicon-nitride ceramic sample of FIG. 7 after compensation for optical attenuation along depth, in accordance with features of the present invention.

In FIG. 7, signal intensity in the z-direction decreases with the depth z, because the intensity of the light traveling in a material is governed by an exponential decay with the travel distance (or depth z in the present case), i.e., $$I = I_0 e^{-\alpha}, \qquad (3)$$

where/and $I_0$ are intensities at depth z and depth z=0, respectively, and α is the linear attenuation coefficient of the sample material and which can be measured as shown in Sun et al, see supra. Under ideal conditions (and ignoring effects due to the material's refractive index), if the value of every pixel is multiplied by a factor of $e^{2\alpha}$ according to its z-position in the image data, the effect of intensity decay in the back-scattered light within the subsurface will be compensated. The factor of 2 comes from the fact that both incident and back-scattered beams travel a depth of z, thus a total decay distance of 2 z. FIG. 8 is a processed image of FIG. 7 after compensation for optical attenuation along the depth z. It is apparent that the back-scattering intensity in FIG. 8 becomes uniform along the z-direction. However, this compensation operation can only be performed to the depth 44 where signal to noise ratio is relatively high. The data become noisy at z=100 µm as described above.

The bright regions in FIG. 8 correspond to regions of low mass density within the materials: air pockets, fault lines or cracks, interfaces, porosity, etc.

Alternate Embodiment

CPCM detection depth depends on the optical penetration depth of materials. It is desirable to detect as deeply as possible. Optical penetration depth is determined by the material's optical properties that are functions of the impinging light's wavelength. For ceramics, for example, the penetration depth typically increases with increasing wavelength. By using a solid-state tunable-wavelength laser, such as a Ti:Sapphire laser which has a tunable range of 0.7–1 micron, optical penetration depth in materials can be increased and optimized. Integrating a Ti:Sapphire laser into a CPCM system is shown in FIG. 9.

Biological materials such as tissues typically have lower optical attenuation in the near-infrared spectrum (e.g., in wavelengths of 0.8–1 micron). Thus a CPCM device with a tunable-wavelength laser may optimize the detection range for biological materials.

The CPCM schematic in the first embodiment (FIG. 2) is based on a x-y-z stage unit that is slow for 3D raster scan.

An alternative would be to use a laser scan system, as shown in FIG. 9. A CPCM device using a beam-scan unit (E.g. a system similar to ones used in bar-code scanning where the laser beam is made to scan a surface as it reflects from a spinning mirror) is fast and allows for real-time optical imaging. In addition, a laser-scan system does not require the sample to be moved (or it only need be moved slowly in the axial z direction) during scans. The laser-scan unit 90 is an x-y scanner in the CPCM schematic of FIG. 9. This system can perform real-time imaging of subsurface 3D micro-structure.

In practice, one may combine features of the two embodiments outlined supra, and devise a wide variety of embodiments.

The foregoing description is for purposes of illustration only and is not intended to limit the scope of protection accorded this invention. The present invention may be presented in other specific embodiments without departing from the essential attributes of the present invention. It is apparent that many modifications, substitutions, and additions may be made to the preferred embodiment while remaining within the scope of the appended claims, which should be interpreted as broadly as possible.

The invention claimed is:

1. A method for depth-resolved detection of subsurface micro-structure and features in a sample, said method comprising:
   a) producing a first illumination of the sample with light possessing polarization in a first direction of polarization creating a first diffraction limited focal point within the sample;
   b) measuring light intensity emanating from the first diffraction limited focal point resulting from said first illumination that is polarized in a second direction of polarization;
   c) changing the relative position and orientation of the first diffraction limited focal point and the sample in one or more directions;
   d) producing a second illumination of the sample with light possessing polarization in the first direction of polarization creating a second diffraction limited focal point directed within the sample;
   e) measuring light intensity emanating from the second diffraction limited focal point resulting from said second illumination that is polarized in the second direction of polarization; and
   f) multiplying the measured light intensity emanating from said first diffraction limited focal point by a factor compensating for attenuation of light within said sample material;
   g) multiplying the measured light intensity emanating from said second diffraction limited focal point by a factor compensating for attenuation of light within said sample;
   h) comparing emanating light intensity between said first diffraction limited focal point and said second diffraction limited focal point.

2. The method as recited in claim 1 wherein said first illumination and said second illumination are provided by a laser.

3. The method as recited in claim 1 wherein said first illumination and said second illumination are constricted to emanate from a polarization-maintaining optical fiber creating a point source and wherein the diameter of the optical fiber is between 1–10 microns.

4. The method as recited in claim 1 wherein steps c) through f) are repeated to obtain multiple positions and orientations of the sample and wherein the emanating light intensity with said second direction of polarization is measured as a function of said positions and orientations.

5. The method as recited in claim 3 wherein said constricted illuminating light is:
   a) expanded by an expanding lens;
   b) traversed through a polarized beam splitter; and
   c) focused by a focusing lens creating said first diffraction limited focal point and said second diffraction limited focal point within the sample.

6. The method as recited in claim 1 wherein said measuring utilizes an optical detector assembly.

7. The method as recited in claim 1 wherein the deflected beam is redirected to successive spots on the sample by means of a laser scan system.

8. The method as recited in claim 1 wherein said subsurface micro-structure is detected through enhancement of the light intensity emanating from the material with said second direction of polarization.

9. A device for depth-resolved detection of subsurface micro-structure and features in a sample, said device comprising:
   a) an initial beam of light polarized in a first direction;
   b) a stage that is movable and orientable in one or more directions; wherein said stage is in optical communication with said initial beam;
   c) means to deflect said initial beam creating a diffraction limited focal point within said sample mounted on the stage so as to produce an illumination of the sample at various three-dimensional locations within said sample;
   d) means to select light emanating from said illumination when said emanating light has a second direction of polarization and is from said diffraction limited focal point;
   e) means to measure the selected light intensity emanating directly from the diffraction limited focal point;
   f) means to compensate the measured emanating light intensity for attenuation of light within said sample.

10. The device as recited in claim 9 wherein said initial beam is provided by a laser and is constricted to emanate from a polarization-maintaining optical fiber creating a point source, wherein the diameter of the optical fiber is between 1–10 microns.

11. The device as recited in claim 9 wherein said initial beam is expanded by a first lens; said deflected beam is focused by a second lens creating said diffraction limited focal point below the surface of the sample; and said light emanating from the diffraction limited focal point is focused on said measuring means by a third lens.

12. The device as recited in claim 9 wherein said deflection means and said selection means are combined in a polarized beam splitter.

13. The device as recited in claim 9 wherein said measuring means comprises a pinhole and an optical detector assembly.

14. The device as recited in claim 9 wherein said initial beam, deflecting means, selecting means, moving means, orienting means, and measuring means are held in a fixed relation with respect to each other.

15. The device as recited in claim 9 further comprising:
   a) means to redirect the diffraction limited focal point beam to successive spots within the sample by a laser scan system; and
   b) means to compare the emanating light intensity from said successive spots.

16. The device as recited in claim 9 further comprising means to compare the measured emanating light intensity from successive illuminations when the location and orientation of the illumination on the sample is changed.

17. A device for depth-resolved detection of sub-surface micro-structure and features in a sample, said device comprising:
- a) a laser producing a beam of light polarized in a first polarization direction;
- b) an optical fiber transmitting said beam while maintaining said first polarization direction such that said beam exits from said fiber as from a point like source, wherein the diameter of the optical fiber is between 1–10 microns;
- c) a first lens expanding said beam;
- d) a polarized beam splitter deflecting said beam toward a sample;
- e) a second lens focusing said deflected beam creating a diffraction limited focal point below the surface of said sample;
- f) a stage supporting said sample, said stage movable and orientable in one or more directions so as to vary positions and orientations of the sample relative to the deflected beam, said sample so mounted on said stage in a first stage position and orientation that light scattered from said sample is directed toward said second lens;
- g) said second lens collecting said scattered light and directing said scattered light toward the polarized beam splitter;
- h) said polarized beam splitter adapted so as to transmit only a portion of the scattered light that is polarized in a second direction of polarization distinct from said first direction of polarization;
- i) a third lens focusing said transmitted light through a diffraction limited pinhole onto a detector assembly adapted to measure the transmitted light from the diffraction limited focal point as a function of said stage motion and orientation;
- j) means to compensate the measured light transmitted from the diffraction limited focal point for attenuation of light within said sample;

wherein said laser, optical fiber, first lens, polarized beam splitter, second lens, diffraction limited focal point, stage, third lens, pinhole, and detector assembly are held in a fixed relation with respect to each other.

18. The device as recited in claim 17 wherein the deflected beam is redirected to successive spots on the sample by a laser scan system.

19. The device as recited in claim 17 further comprising means to digitize, store, and visualize the measurements made by said detector assembly.

20. The method as recited in claim 1 wherein steps c) through f) are repeated to obtain multiple measurements and the stage is moved in three-dimensions in a raster fashion; and a means to create a three-dimensional image from the multiple measurements.

* * * * *

UNITED STATES PATENT AND TRADEMARK OFFICE
CERTIFICATE OF CORRECTION

PATENT NO.         : 7,042,556 B1
APPLICATION NO. : 10/731772
DATED              : May 9, 2006
INVENTOR(S)       : Jiangang Sun It is certified that error appears in the above-identified patent and that said Letters Patent is hereby corrected as shown below:

On the Title Page, Item (74) should read:
Item (74)  Attorney, Agent, or Firm -- Michael J. Dobbs; Brian J. Lally; Paul A. Gottlieb Signed and Sealed this Twenty-second Day of August, 2006

JON W. DUDAS
*Director of the United States Patent and Trademark Office*